United States Patent
Fuji et al.

(10) Patent No.: US 9,314,646 B2
(45) Date of Patent: Apr. 19, 2016

(54) SKIN DOSE EVALUATION SUPPORT APPARATUS AND TREATMENT PLANNING APPARATUS

(75) Inventors: Hideki Fuji, Tokyo (JP); Yasuyuki Takatani, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 198 days.

(21) Appl. No.: 14/118,729

(22) PCT Filed: Aug. 17, 2011

(86) PCT No.: PCT/JP2011/068604
§ 371 (c)(1),
(2), (4) Date: Nov. 19, 2013

(87) PCT Pub. No.: WO2013/024534
PCT Pub. Date: Feb. 21, 2013

(65) Prior Publication Data
US 2014/0094642 A1 Apr. 3, 2014

(51) Int. Cl.
*G06K 9/00* (2006.01)
*A61N 5/10* (2006.01)
(Continued)

(52) U.S. Cl.
CPC .............. *A61N 5/1039* (2013.01); *A61B 6/032* (2013.01); *A61B 6/466* (2013.01); *A61N 5/103* (2013.01); *A61N 5/1031* (2013.01); *A61N 5/1071* (2013.01); *A61N 2005/1074* (2013.01)

(58) Field of Classification Search
CPC ..................................... A61N 5/00; A61B 6/00
USPC ........ 382/128–134; 600/1, 29, 300, 306, 407, 600/425, 556, 557; 378/65, 97, 108; 250/370.07, 390.03
See application file for complete search history.

(56) References Cited

U.S. PATENT DOCUMENTS

| | | | | |
|---|---|---|---|---|
| 4,455,609 A | * | 6/1984 | Inamura | .................... G01T 1/02 250/370.07 |
| 2003/0147495 A1 | | 8/2003 | Kato et al. | |

(Continued)

FOREIGN PATENT DOCUMENTS

| | | |
|---|---|---|
| JP | 8-280824 A | 10/1996 |
| JP | 10-146395 A | 6/1998 |

(Continued)

OTHER PUBLICATIONS

International Search Report (PCT/ISA/210) mailed on Oct. 25, 2011, by the Japanese Patent Office as the International Searching Authority for International Application No. PCT/JP2011/068604.

(Continued)

*Primary Examiner* — Abolfazl Tabatabai
(74) *Attorney, Agent, or Firm* — Buchanan Ingersoll & Rooney PC

(57) ABSTRACT

A skin dose evaluation support apparatus is provided with a skin region contour creation unit that creates skin region information including the boundary coordinates of a skin region, based on image data to be inputted when a treatment plan for a radiation therapy for a patient is created; and a display calculation unit that extracts a skin dose in a skin region, based on dose distribution data calculated by a dose distribution calculation unit of a treatment planning apparatus and the skin region information, and creates display data for displaying the extracted skin dose in a predetermined display format.

16 Claims, 8 Drawing Sheets

(51) Int. Cl.
  *A61B 6/03* (2006.01)
  *A61B 6/00* (2006.01)
  *H05G 1/42* (2006.01)
  *H05G 1/44* (2006.01)
  *G01T 1/02* (2006.01)

(56) References Cited

U.S. PATENT DOCUMENTS

| | | |
|---|---|---|
| 2005/0207531 A1 | 9/2005 | Dempsey et al. |
| 2008/0081991 A1 | 4/2008 | West et al. |
| 2009/0003527 A1 | 1/2009 | Hoornaert et al. |
| 2010/0069895 A1* | 3/2010 | Zemmouri et al. ............... 606/9 |
| 2010/0228116 A1 | 9/2010 | Lu et al. |

FOREIGN PATENT DOCUMENTS

| | | |
|---|---|---|
| JP | 10-244013 A | 9/1998 |
| JP | 10-309324 A | 11/1998 |
| JP | 2001-29490 A | 2/2001 |
| JP | 2007-175323 A | 7/2007 |
| JP | 2008-80131 A | 4/2008 |
| JP | 2008-113721 A | 5/2008 |
| JP | 2009-523049 A | 6/2009 |
| WO | 2005/072825 A1 | 8/2005 |
| WO | WO 2007/080522 A1 | 7/2007 |
| WO | 2010/102068 A2 | 9/2010 |

OTHER PUBLICATIONS

Chugh K. et al., "A Computer-Graphic Display for Real-Time Operator Feedback during Interventional X-Ray Procedures," Proceedings of the Spie, 2004, V5367, pp. 464-473.
Den Boer Ad et al., "Real-Time Quantification and Display of Skin Radiation During Coronary Angiography and Intervention, Circulation," Oct. 9, 2001, V104, pp. 1779-1784.
Abstract for Meyer Philippe et al., "Feasibility of a semiconductor dosimeter to monitor skin dose in interventional radiology," Medical Physics, Oct. 2001, V28 N10, pp. 2002-2006.
Miller L. Donald et al., "Minimizing Radiation-induced Skin Injury in Interventional Radiology Procedures," Radiology, Nov. 2002, V225, pp. 329-336.
European Search Report dated Feb. 23, 2015 issued in corresponding European Patent Appln. No. 11870949.2 (5 pages).
Office Action issued on Apr. 9, 2014, by the Taiwanese Patent Office in corresponding Taiwanese Patent Application No. 101107856, and an English Translation of the Office Action. (12 pages).
Office Action (Notification of Reason for Refusal) issued on Aug. 19, 2014, by the Japanese Patent Office in corresponding Japanese Patent Application No. 2013-528884 and an English translation of the Office Action. (13 pages).
First Chinese Office Action issued by the Chinese Patent Office on Jul. 1, 2015 in corresponding Chinese Patent Application No. 2011800724633, with full English translation (18 pages).

* cited by examiner

SKIN DOSE EVALUATION SUPPORT APPARATUS AND TREATMENT PLANNING APPARATUS

TECHNICAL FIELD

The present invention relates to creation of a treatment plan for a radiation therapy system and more particularly to a skin dose evaluation support apparatus that makes it possible to evaluate a skin dose and a surface region dose on a major organ.

BACKGROUND ART

In the case of radiation therapy in which treatment is implemented by use of radiations, it is required that a dose with which a sufficient therapy effect is demonstrated is provided to a focus such as a cancer while normal tissues are suppressed as much as possible from being exposed to the radiations. Accordingly, in general, a treatment plan is required in which before a therapy is implemented, it is determined and decided from which direction and at which intensity level radiations should be irradiated, by use of image data taken by a diagnostic imaging apparatus such as an X-ray CT apparatus and based on the result of a dose distribution simulation or the like.

In general, such a treatment plan is implemented by use of software that operates on a computer system. In a treatment plan, at first, there is set a three-dimensional region for a focus and its peripheral normal tissues on which attention is to be placed, by utilizing image data, and then the coordinates thereof are stored in a memory. Next, based on an irradiation coverage (referred to as an irradiation field) determined in accordance with the size of the focus and a tentatively decided irradiation direction and irradiation intensity, a three-dimensional dose distribution in a human body is calculated pursuant to a given physical model and by use of the image data.

The result obtained in such a manner is evaluated by use of various kinds of evaluation methods. The evaluation methods include, for example, a DVH (Dose Volume Histogram) which is a graph representing a relationship between a dose and the volume of a tissue having the value of the dose, an isodose chart in which a dose distribution is superimposed on a human body tomogram, a three-dimensional display in which a dose distribution, which is kept as three-dimensional data, is superimposed on a human body tissue and the superimposed chart is expressed in a translucent and a three-dimensional manner, and the like. In the case where it is determined through these methods that the dose distribution is a desirable one, the tentatively decided irradiation direction and irradiation intensity are adopted for the therapy; otherwise, the irradiation direction and the irradiation intensity are again decided and the dose distribution is calculated once again; then, the result is evaluated. In general, in a treatment plan, such work is repeated so that the irradiation direction and the irradiation intensity to be adopted for a therapy are decided.

Patent Document 1 discloses a three-dimensional image processing method through which in order to visually evaluate a treatment plan, there is outputted a three-dimensional display where a human body tissue and a dose distribution, which is obtained by a calculation, are superimposed on each other. A three-dimensional display in which a dose distribution obtained through a calculation is superimposed on a human body tissue has been rendered with the dose distribution as a region of 10% or larger target dose or with the dose distribution as a region of 95% or larger target dose, when the maximum dose value is 100% target dose; in other words, the three-dimensional display has been rendered with different dose-distribution rendering conditions. As a result, for example, it has been observed that a focus is included in the region of 10% or larger target dose and is slightly out of the region of 95% or larger target dose, so that the dose for the focus has been evaluated.

PRIOR ART REFERENCE

Patent Document

[Patent Document 1] Japanese Patent Application Laid-Open No. H10-244013 (paragraph [0007], FIG. 10)

DISCLOSURE OF THE INVENTION

Problems to be Solved by the Invention

In recent years, when a treatment plan is created, simulations have been implemented while the irradiation direction and irradiation intensity are contrived in a treatment plan creation process so that in terms of QOL (Quality of Life), a skin inflammation, which is a side effect of radiation irradiation, can be reduced as much as possible. In the case Where a treatment plan is created in such a way that a skin inflammation can be reduced as much as possible, it is important that a skin dose in the created treatment plan can appropriately be evaluated. When a treatment plan is created, simulation is repeated, as described above, until a desirable result is obtained; therefore, in order to appropriately change the conditions for the simulation, it is important that a skin dose can accurately and intuitively be grasped.

Conventional three-dimensional image processing methods are capable of visually evaluating a dose for a focus but are not capable of visually evaluating a skin dose, which is a dose for a skin.

The present invention has been implemented in order to solve the foregoing problems; the objective thereof is to obtain a skin dose evaluation support apparatus that can accurately and intuitively grasp a skin dose when a treatment plan is created.

Means for Solving the Problems

A skin dose evaluation support apparatus is provided with a skin region contour creation unit that creates skin region information including the boundary coordinates of a skin region, based on image data to be inputted when a treatment plan for a radiation therapy for a patient is created; and a display calculation unit that extracts the skin dose in the skin region, based on dose distribution data calculated by a dose distribution calculation unit of a treatment planning apparatus and the skin region information, and creates display data for displaying the extracted skin dose in a predetermined display format.

Advantage of the Invention

A skin dose evaluation support apparatus according to the present invention extracts a skin dose in a skin region, based on dose distribution data calculated by a dose distribution calculation unit of a treatment planning apparatus and skin region information created by a skin region contour creation unit, and displays the extracted skin dose in a predetermined display format; therefore, the skin dose can accurately and intuitively be grasped when a treatment plan is created.

BEST MODE FOR CARRYING OUT THE INVENTION

Embodiment 1

Figure 1:
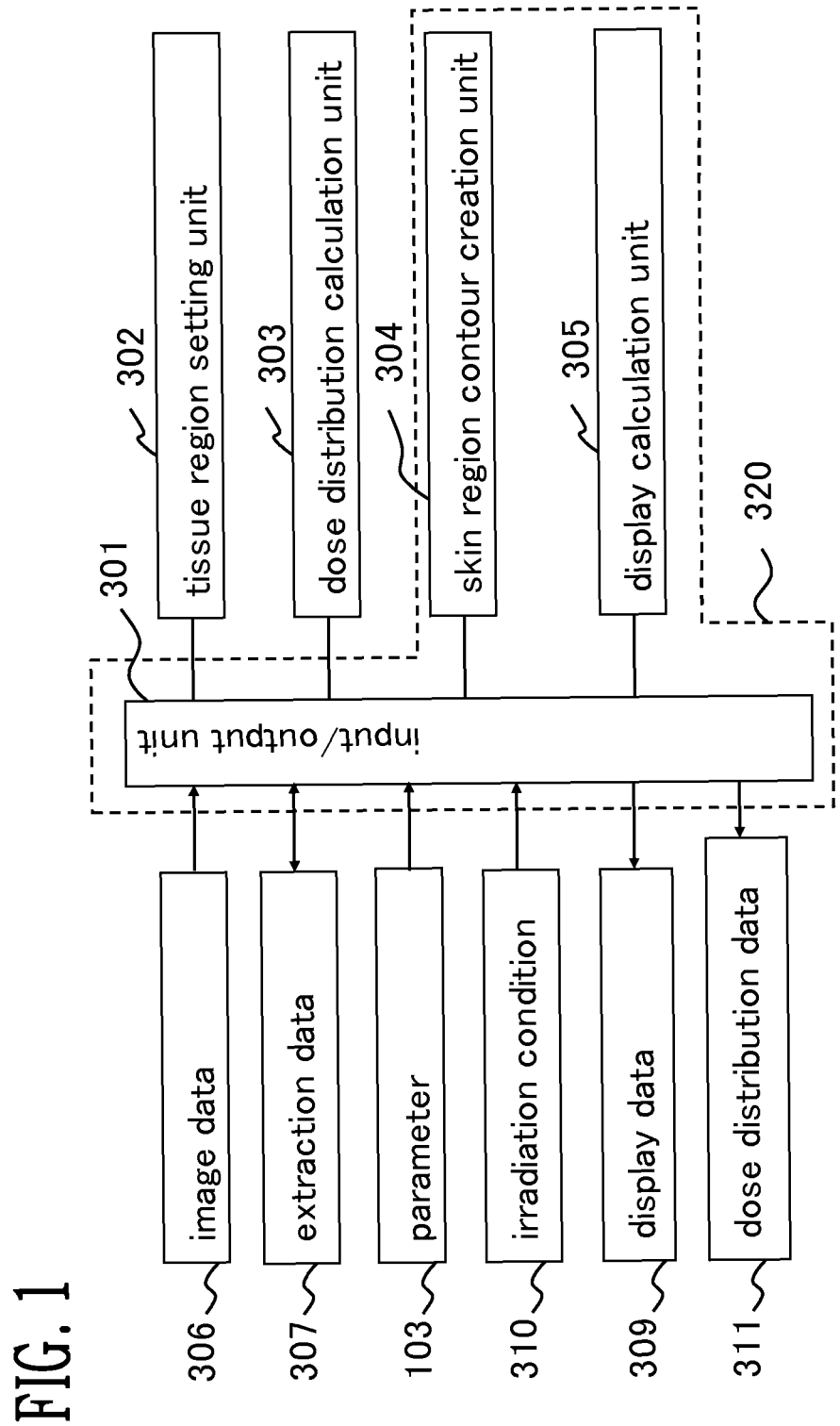
FIG. 1 is a diagram representing the configurations of a skin dose evaluation support apparatus and a treatment planning apparatus according to Embodiment 1 of the present invention.
Figure 2:
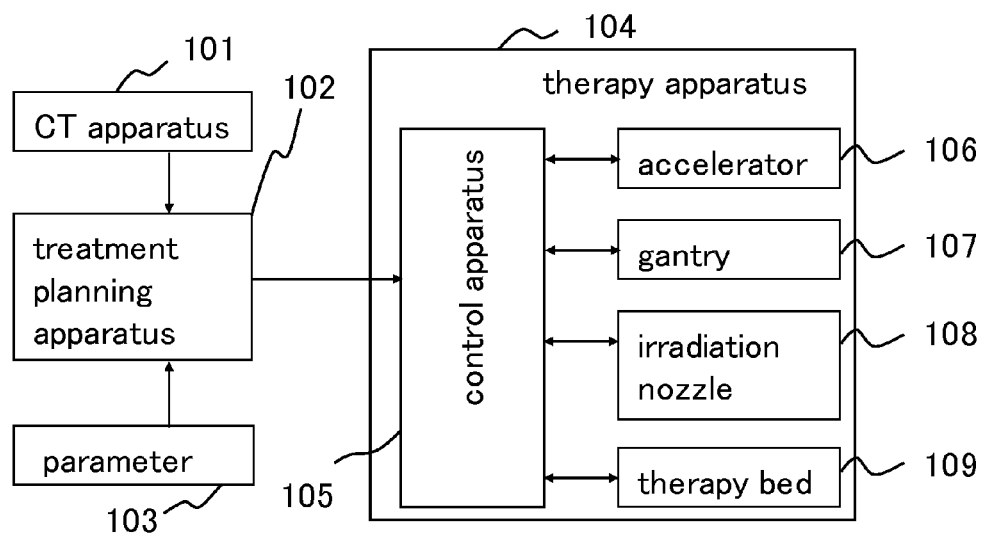
FIG. 2 is a diagram representing a radiation therapy system provided with a skin dose evaluation support apparatus according to Embodiment 1 of the present invention.
Figure 3:
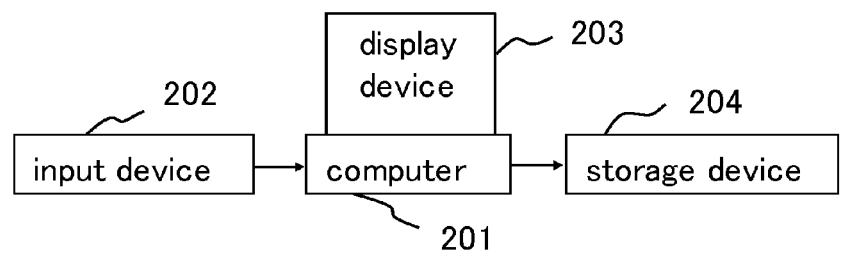
FIG. 3 is a diagram representing a computer system included in the treatment planning apparatus in FIG. 2.

FIG. 1 is a diagram representing the configurations of a skin dose evaluation support apparatus and a treatment planning apparatus according to Embodiment 1 of the present invention. FIG. 2 is a diagram representing a radiation therapy system provided with a skin dose evaluation support apparatus according to Embodiment 1 of the present invention. FIG. 3 is a diagram representing a computer system included in the treatment planning apparatus in FIG. 2. A radiation therapy system will be explained with reference to FIG. 2. A radiation therapy system according to the present invention is configured with a CT apparatus 101, a treatment planning apparatus 102, and a therapy apparatus 104. The therapy apparatus 104 is configured with an accelerator 106, a gantry 107, an irradiation nozzle 108, a therapy bed 109, and a control apparatus 105 that controls these apparatuses.

The CT apparatus 101 obtains a human body tomogram of a human body, which is a therapy subject. The human body tomogram obtained by the CT apparatus 101 is inputted to the treatment planning apparatus 102. The treatment planning apparatus 102 calculates a dose distribution based on various kinds of parameters 103 and evaluates and determines the result. These parameters 103 are changed several times, so that the most appropriate irradiation condition is determined. The determined irradiation condition is inputted to the control apparatus 105 in the therapy apparatus 104.

A computer system included in the treatment planning apparatus 102 will be explained with reference to FIG. 3. The treatment planning apparatus 102 is configured with a computer main body 201, an input device 202 for inputting an instruction of an operator and data such as image data, a display device 203 for displaying results, and a storage device 204 for storing treatment planning software itself and output results.

The skin dose evaluation support apparatus according to the present invention can be realized, for example, as software that operates on the treatment planning apparatus 102 or the like, and can be distributed through a portable recording medium such as a flexible disk or a CD-ROM or through a means such as a network or the like.

The skin dose evaluation support apparatus and the treatment planning apparatus according to Embodiment 1 of the present invention will be explained with reference to FIG. 1. The treatment planning apparatus 102 is provided with processing units such as a tissue region setting unit 302, a skin region contour creation unit 304, a dose distribution calculation unit 303, and a display calculation unit 305; by way of an input/output unit 301, image data 306, extraction data 307, the parameters 103, an irradiation condition 310, display data 309, dose distribution data 311, and the like are inputted to or outputted from the storage device 204 and the display device 203 by each of the processing units. The input/output unit 301, the skin region contour creation unit 304, and the display calculation unit 305 configure a skin dose evaluation support apparatus 320.

Next, there will be explained the details of the processing units that perform treatment planning in the treatment planning apparatus 102. In the following processing, the image data 306, which is taken by the CT apparatus 101 or the like, is utilized. The image data herein denotes image densities stored in a three-dimensional matrix configured with voxels.

When treatment planning is performed, the image data 306 is inputted, at first. Then, the extraction area and the like are specified by use of the parameters 103; the extraction result is obtained by the tissue region setting unit 302; then, the result is stored, as the extraction data 307, in the storage device 204. For example, when tissue region setting is implemented, a single focus and a plurality of major organs are set.

The tissue region setting unit 302 is a unit which obtains a body contour 401, a focus 403, and the three-dimensional coordinates of major organs 404, 405, and the like from the image data 306, which is a three-dimensional image stored in the three-dimensional matrix configured with voxels. For example, the body contour 401, the focus 403, and the major organs 404 and 405 are illustrated in a human body cross-sectional view in FIG. 4. The tissue region setting unit 302 sets a tissue region through a semiautomatic extraction method such as a method in which an image density threshold value is utilized or a region expansion method in which link information among tissues is utilized or through a region specifying method in which a person traces a tissue region to be focused in each slice image outputted to a display device.

The skin region contour creation unit 304 automatically creates a skin region contour 402, which is a boundary of a skin region, while a user is not aware of the creation. In addition, the skin region contour creation unit 304 creates skin region information, assuming that the region surrounded by the body contour 401 and the skin region contour 402 is a skin region. Specifically, when the user activates the tissue region setting unit 302 so as to create the body contour 401, the skin region contour 402, which is an inner contour of the skin, is automatically created inside the body contour 401 (several pixels inward from the body contour). The skin region information items are the three-dimensional coordinates of a skin region and includes at least the three-dimensional coordinates (boundary coordinates) of the skin region contour 402. It can be changed by use of the parameters 103 by how many pixels inward from the body contour 401 the skin region contour 402 is created. Moreover, also in the case where the region of a skin should be made partially thicker or thinner, the skin region can be modified when in an editing mode, the user traces the skin region contour 402, which is to be modified, in each slice image outputted to the display device 203. In such a manner as described above, the editing mode makes it possible to adjust the thickness, depending on a patient or a body part.

The dose distribution calculation unit 303 calculates a dose distribution through a dose distribution calculation method based on the physical model for each radiation. The dose distribution calculation for a particle beam such as a proton beam or a carbon beam is performed, for example, in the broad beam method; the dose distribution calculation for an X ray is performed, for example, in the TPR method. The dose distribution calculation unit 303 implements a dose distribution calculation and outputs the dose distribution, as voxel data stored in a three-dimensional matrix. In the case where there exist two or more irradiation directions, a dose distribution calculation is performed for each of the two or more irradiation directions, and the dose distribution for each irradiation direction is outputted.

For the purpose of performing a dose distribution calculation, each time the irradiation condition 310 is inputted, processing by the dose distribution calculation unit 303 is repeatedly performed; the result is evaluated, so that the last irradiation condition 310 and the dose distribution data 311 are obtained and stored in the storage device 204. In this process, the display calculation unit 305 outputs the condition of the dose distribution, as the display data 309, to the display device 203; the condition of the dose distribution is displayed on the display device 203.

The display calculation unit 305 creates display data items such as a three-dimensional display, a cross section isodose chart display, a DVH display, and the like corresponding to a focus, an organ to be focused, a skin region, and the like. In the case where the skin dose in a skin region is displayed in a predetermined display format, the display calculation unit 305 extracts the skin dose in a skin region, based on the dose distribution data 311 calculated by the dose distribution calculation unit 303 and the skin region information created by the tissue region setting unit 302; then, the display calculation unit 305 creates display data for displaying the extracted skin dose in the predetermined display format. As is the case with a conventional display method, in a three-dimensional display, a human body tissue and a dose distribution, which are three-dimensional distribution data items, are superimposed on each other; then, both of them are translucently displayed on a two-dimensional projection plane. This kind of three-dimensional display makes it possible to intuitively grasp the positional relationship between a human body tissue and a dose distribution in the three-dimensional space. As is the case with a conventional display method, a cross section isodose chart display for displaying an isodose chart in a specified cross section, a DVH display for displaying a DVH, and the like are also displayed.

Figure 5:
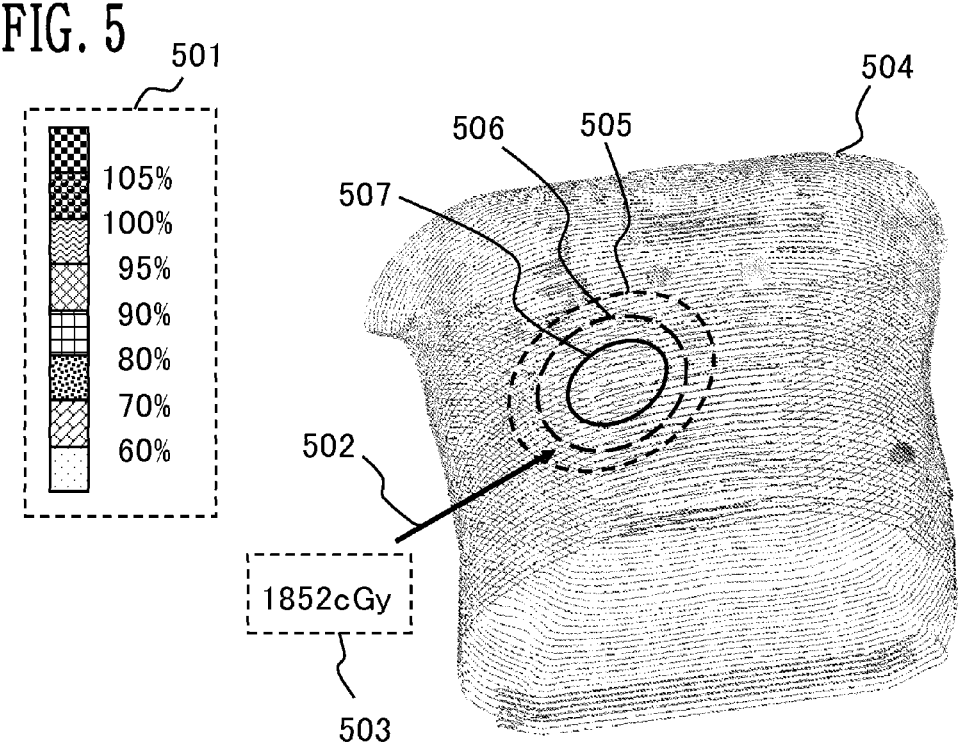
FIG. 5 is a view illustrating a dose distribution of skin doses in a three-dimensional display.

A three-dimensional display of a dose on a skin surface in the present invention will be explained. FIG. 5 is a view illustrating a dose distribution of skin doses in a three-dimensional display. FIG. 5 is an example representing a bird's eye view at a time when a body contour assembly 504 that is a human body in which two or more body contours are laid on one another and which is displayed in a three-dimensional manner is obliquely viewed. As illustrated in FIG. 5, in a three-dimensional display, a dose distribution, which is three-dimensional distribution data, is superimposed in a three-dimensional manner on a human body image, which is rendered in a three-dimensional manner; then, both of them are translucently displayed on a two-dimensional projection plane. The body contour assembly 504 is an assembly of contours on two or more cross sections. Isodose lines 505, 506, and 507 represent the doses on the skin surface. Each of the isodose lines 505, 506, and 507 is obtained by connecting with a line the portions having a single and the same relative dose value at a time when doses in each slice image of the image data 306 are normalized with respect to the maximum dose (100%). The isodose line 505 is a line that denotes that the relative dose in the skin region is larger than 0%, e.g., 0.1%; the isodose line 506 is a line that denotes that the relative dose in the skin region is 60%; the isodose line 507 is a line that denotes that the relative dose in the skin region is 70%.

Reference numeral 501 denotes a dose indicator. In FIG. 5, the dose indicator 501 is an indicator for relative doses. The region between the isodose line 505 and the isodose line 506 is a dose region having a relative dose from over 0% to fewer than 60%, including the data on the isodose line 505. The region between the isodose line 506 and the isodose line 507 is a dose region having a relative dose from 60% to fewer than 70%, including the data on the isodose line 506. The region surrounded by the isodose line 507 is a dose region having a relative dose from 70% to fewer than 80%, including the data on the isodose line 507. In FIG. 5, in order to prevent the drawing from becoming complicated, the pattern for representing the regions corresponding to relative doses is omitted.

As represented in FIG. 5, the three-dimensional display makes it possible to intuitively grasp the positional relationship between a skin and a skin dose distribution in the three-dimensional space. A three-dimensional human body is represented by the body contour assembly 504, which is an assembly of contours on two or more cross sections; therefore, because the display of a skin and a dose distribution does not mingle with the display of another human body tissue, the positional relationship between the skin and the skin dose distribution can clearly be grasped. Because a region divided based on the numeral value, for example, the region having a relative dose from A % to fewer than B % is displayed, effect evaluation on a skin dose can quantitatively be performed. By specifying each point by a pointer 502, it is made possible to display the dose 503 at the point; when the pointer 502 specifies a display point, the value of the skin dose corresponding to the display point is displayed on the display device 203. In such a manner as described above, the dose at each point can directly be grasped. The display of the dose indicator 501 may be an absolute dose display (cGy). In addition, as the reference of a relative dose, the dose at an isocenter may be utilized.

Figure 6:
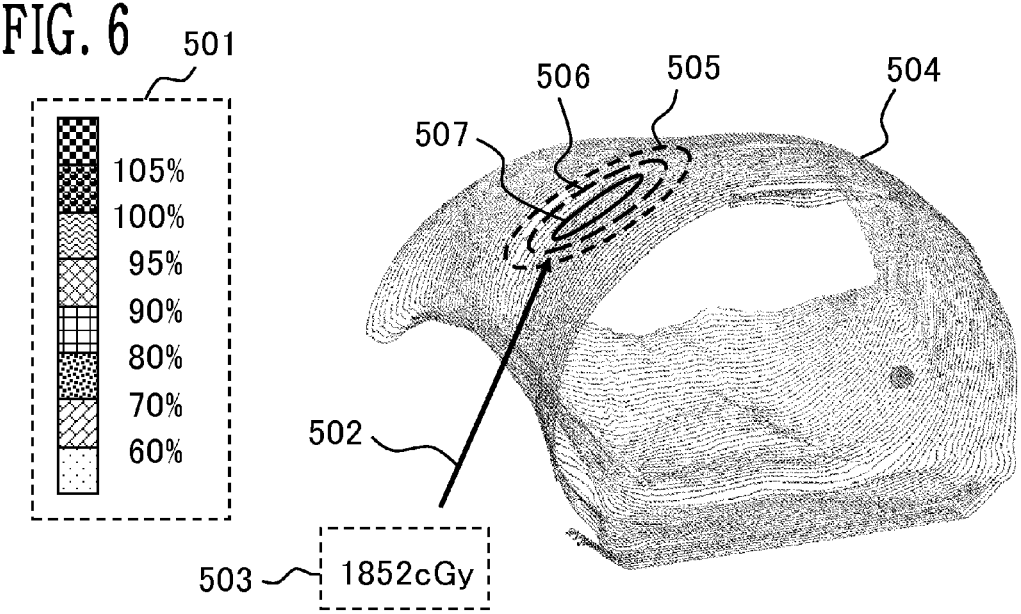
FIG. 6 is a view illustrating the dose distribution of skin doses in a three-dimensional display in FIG. 5 when the viewing angle is changed.

FIG. 6 is the three-dimensional display in FIG. 5 when the viewing angle is changed. In the three-dimensional display, the user can freely change the viewing angle through manipulating a mouse or the like. As described above, the user can ascertain the dose distribution on a skin surface from an arbitrary direction.

Figure 4:
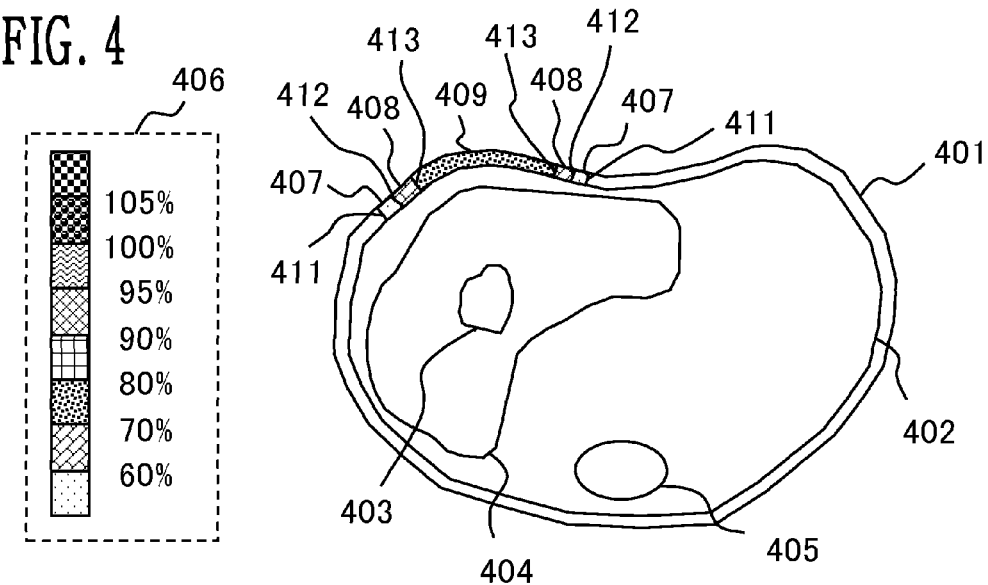
FIG. 4 is a view illustrating the dose distribution of skin doses on a specified cross section.

A cross section isodose chart display of a skin region according to the present invention will be explained. FIG. 4 is a view illustrating the dose distribution of skin doses on a specified cross section. Isodose lines 411, 412, and 413 represent the doses on the skin surface. As is the case with the explanation in FIG. 5, each of the isodose lines 411, 412, and 413 is obtained by connecting with a line the portions having a single and the same relative dose value at a time when doses in each slice plane of the image data 306 are normalized with respect to the maximum dose (100%). The isodose line 411 is a line that denotes that the relative dose in the skin region is larger than 0%, e.g., 0.1%; the isodose line 412 is a line that denotes that the relative dose in the skin region is 60%; the isodose line 413 is a line that denotes that the relative dose in the skin region is 70%.

Reference numeral 406 denotes a dose indicator. In FIG. 4, the dose indicator 406 is an indicator for relative doses. The region between the isodose line 411 and the isodose line 412 is a dose region having a relative dose from over 0% to fewer than 60%, including the data on the isodose line 411, and corresponds to the dose region 407 in FIG. 4. The region between the isodose line 412 and the isodose line 413 is a dose region having a relative dose from 60% to fewer than 70%, including the data on the isodose line 412, and corresponds to the dose region 408 in FIG. 4. The region surrounded by the isodose line 413 is a dose region having a relative dose from 70% to fewer than 80%, including the data on the isodose line 413, and corresponds to the dose region 409 in FIG. 4.

As illustrated in FIG. 4, the cross section isodose chart display makes it possible to intuitively grasp the positional relationship between a skin and a skin dose distribution in the human body cross-sectional view. Because a region divided based on the numeral value, for example, the region having a relative dose from A % to fewer than B % is displayed, effect evaluation on a skin dose can quantitatively be performed. As is the case with the respective three-dimensional displays in FIGS. 5 and 6, by specifying each point by a pointer, it is made possible to display the dose at the point; thus, the dose at each point can intuitively be grasped with a numeral value. The display of the dose indicator 406 may be an absolute dose display (cGy). In addition, as the reference of a relative dose, the dose at an isocenter may be utilized. An example has been explained in which different display patterns are assigned to the respective relative dose regions; however, in fact, it is preferable that the display patterns are expressed with different colors. In the drawings herein, display with different colors cannot be implemented; therefore, display with different patterns has been implemented.

Figure 7:
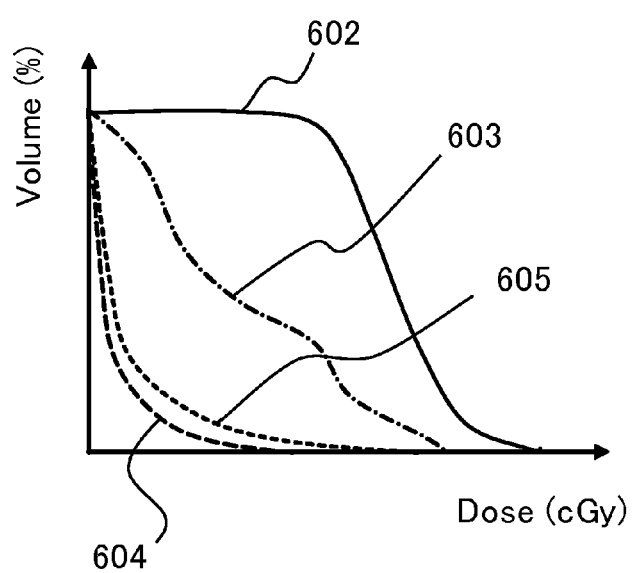
FIG. 7 is a graph representing a plurality of DVHs including a skin region DVH.

The DVH display will be explained. When performing a DVH display, the display calculation unit 305 sets the dose on the abscissa and the volume on the ordinate with regard to the focus, the normal tissue, and the whole human body tissue on the image data 306 taken by the CT apparatus 101, for which respective regions are set as represented in FIG. 7; for each dose value, the sum of the whole tissue, that is the same as or larger than the dose value is displayed as a graph. FIG. 7 is a graph representing a plurality of DVHs including a skin region DVH. A DVH characteristic curve 602 represents a characteristic for a region-set focus and is obtained by connecting the vertexes of the respective bars (not shown) of the DVH. A DVH characteristic curve 604 represents a characteristic for a normal tissue; a DVH characteristic curve 605 represents a characteristic for the whole human body tissue. The DVH characteristic curves 602, 604, and 605 are similar to conventional DVH characteristic curves. In the present invention, the display calculation unit 305 can also display a DVH characteristic curve 603 of a defined skin region in the DVH display.

In the case of a DVH display, the scales of the abscissa and the ordinate of a graph can separately be changed. There can also be implemented display in which the abscissa represents not only an absolute dose but also a relative dose (%) normalized with respect to the isocenter or the maximum dose (100%).

A DVH display makes it possible to grasp how much volume of a focus, which is a treatment subject and a target tissue, is irradiated up to a lethal dose or more and to grasp how much volume of a normal tissue is suppressed from being irradiated up to an allowable dose or less. By viewing the DVH of whole human body tissue, it is made possible to know to what extent the dose is scattered to the whole tissue. With a DVH of whole human body tissue, it can be determined that when there exists as much volume as possible in the low-dose region, the treatment plan is a more desirable plan. A DVH display makes it possible to quantitatively evaluate a dose distribution, which is the result of a calculation. In other words, a DVH makes it possible to read a numeral value. As represented in FIG. 7, there can be obtained the information on how much dose (cGy) is irradiated onto how much percentage of the whole volume. Each hospital has its own treatment protocol such as that the region, of a target tissue, onto which what dose (cGy) is irradiated is what percentage of the whole volume, that the region, of a major organ, onto which what dose (cGy) is irradiated is within what percentage of the whole volume, or the like; therefore, quantization such as a DVH display is important.

In the skin dose evaluation support apparatus 320 according to Embodiment 1, as described above, the display calculation unit 305 can also display the DVH characteristic curve 603 of a defined skin region in the DVH display. Because the skin dose evaluation support apparatus 320 can display the DVH characteristic curve 603 of a skin region, information on what dose (cGy) is irradiated onto what percentage of the whole volume of the skin region can be obtained; therefore, the dose distribution, which is the result of the calculation, can quantitatively be evaluated.

Figure 8:
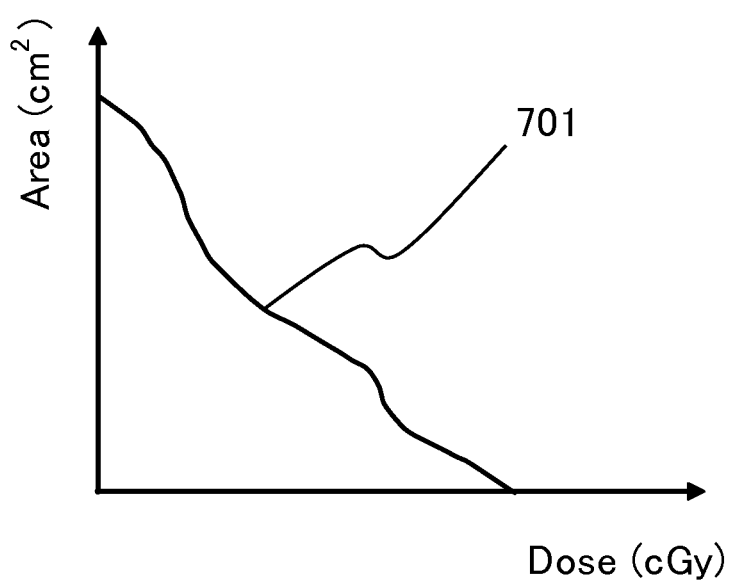
FIG. 8 is a graph representing a relationship between the skin region dose and the skin region area.

When the dose and the area ($cm^2$) are set on the abscissa and the ordinate, respectively, the display calculation unit 305 can also display the area in a skin region where the dose value becomes the same as or larger than a dose value with which the skin region is irradiated; therefore, the skin dose can quantitatively be evaluated. FIG. 8 is a graph representing a relationship between the skin region dose and the skin region area. The relationship between the skin region dose and the skin region area represented in FIG. 8 will herein be referred to as a DAH (Dose Area Histogram). Reference numeral 701 in FIG. 8 denotes a DAH characteristic curve of a defined skin region. A conventional DVH has been an indicator for grasping the relationship between the dose to be irradiated onto a target tissue or a major organ and the volume. However, in the case where as the present invention, a skin dose is evaluated, it is more appropriate that determination is made based on the relationship between the dose and the area than that determination is made based on the relationship between the dose and the volume; therefore, an indicator for grasping the relationship between the dose and the area has been introduced and a function for displaying a DAH has been added to the skin dose evaluation support apparatus 320 according to Embodiment 1.

As a DAH display for displaying a DAH, the area is set on the ordinate, so that quantitative information on what area ($cm^2$) on a skin surface has been irradiated by what skin dose (cGy), i.e., how widely the skin surface has been irradiated can be obtained. For example, the information can be utilized for making a determination on how wide the area is where skin inflammation occurs after an irradiation. Instead of the area ($cm^2$), the area (%) can be set on the ordinate of a DAH display. In the case where the area (%) is set on the ordinate of a DAH display, information on what skin dose (cGy) is irradiated onto what percentage of the whole area of a skin region can be obtained. There can also be implemented display in which the abscissa represents not only an absolute dose but also a relative dose (%) normalized with respect to the isocenter or the maximum dose (100%).

In the case where there exists two or more beams in the three-dimensional display (FIG. 5, FIG. 6), the cross section isodose chart display (FIG. 4), the DVH display (FIG. 7), or the DAH display (FIG. 8), the display calculation unit 305 can also display the dose of each beam, the total dose of specified beams, and the total dose of all beams.

In the skin dose evaluation support apparatus 320 according to Embodiment 1, the display device 203 can display a predetermined display format which display a skin dose visually, specifically, a three-dimensional display, a cross section isodose chart display, a DVH display, and a DAH display. With these displays, the treatment planning apparatus 102 provided with the skin dose evaluation support apparatus 320 makes it possible to accurately and intuitively grasp a skin dose in treatment planning. The treatment planning apparatus 102 makes it possible to accurately and intuitively grasp a skin dose; thus, a treatment plan that can diminish as much skin inflammation as possible can be created. Moreover, the treatment planning apparatus 102 repeats simulations, while appropriately changing the conditions of a treatment plan, in accordance with evaluations based on various kinds of skin-dose displays by the skin dose evaluation support apparatus 320, and can obtain a desirable result through a small number of simulations.

Whether or not a skin inflammation is caused depends to some extent on a divided irradiation or a site; however, the reference is established to some extent in such a manner that a skin inflammation is caused when the skin is exposed to what dose (cGy) or more. Therefore, by creating a skin region and implementing a DVH display or a DAH display, information on what percentage of the region or on what area of the region (cm$^2$) with what dose (cGy) or more exists can be obtained. Evaluation of a skin dose in treatment planning makes it possible to accurately and intuitively grasp in what percentage of the region a skin inflammation is caused; then, the result can be reflected in the treatment plan in such a way that the skin inflammation can be diminished as much as possible.

In the skin dose evaluation support apparatus 320 according to Embodiment 1, the skin region contour creation unit 304 automatically creates a skin region contour; therefore, there can be omitted user's work in which for the image data 306, taken by a CT apparatus, including a hundred and several tens of slice images, an inner contour is expressly defined (set) inside the body contour 401 for each of the slice images in the image data 306. In the case where the work of creating an inner contour for determining a skin region is manually performed, the work takes a long time; therefore, there is posed a problem that it takes an extremely long time to create a treatment plan in which the result of skin-dose evaluation is reflected. Because the skin dose evaluation support apparatus 320 according to Embodiment 1 is provided with the skin region contour creation unit 304, it is made possible to create in a short time an inner contour to determine a skin region, i.e., the skin region contour 402; thus, a treatment plan in which the result of skin-dose evaluation is reflected can be completed in a short time. Because it is made possible to create the skin region contour 402 by the skin region contour creation unit 304 and the editing mode makes it possible to make an adjustment, the skin region contour 402 can accurately be created in a short time.

As described above, the skin dose evaluation support apparatus 320 according to Embodiment 1 is provided with the skin region contour creation unit 304 that creates skin region information including the boundary coordinates of a skin region, based on the image data 306 to be inputted when a radiation-therapy treatment plan for a patient is created and with the display calculation unit 305 that extracts the skin dose in the skin region, based on the dose distribution data 311 calculated by the dose distribution calculation unit 303 of the treatment planning apparatus 102 and the skin region information, and creates the display data 309 for displaying the extracted skin dose in a predetermined display format; therefore, by displaying in a predetermined display format the skin dose in a skin region, which is extracted based on the dose distribution data 311 and the skin region information, it is made possible to visually display the skin dose; therefore, the skin dose can accurately and intuitively be grasped when a treatment plan is created.

The treatment planning apparatus 102 according to Embodiment 1 is provided with the tissue region setting unit 302 that obtains the three-dimensional coordinates of a body contour, a major organ, and a focus, which is a treatment subject, based on the image data 306 of a patient, the dose distribution calculation unit 303 that calculates the distribution of doses on the patient, based on a model in accordance with a radiation utilized in a radiation therapy, and the skin dose evaluation support apparatus 320 that displays on the display device 203 the skin dose in a skin region of the patient; the skin dose evaluation support apparatus 320 is provided with the skin region contour creation unit 304 that creates skin region information including the boundary coordinates of a skin region, based on the image data 306 and with the display calculation unit 305 that extracts the skin dose in the skin region, based on the dose distribution data 311 calculated by the dose distribution calculation unit 303 and the skin region information, and creates the display data 309 for displaying the extracted skin dose in a predetermined display format. As a result, the skin dose evaluation support apparatus 320 makes it possible to accurately and intuitively grasp a skin dose; thus, a treatment plan that can diminish as much skin inflammation as possible can be created. Moreover, the treatment planning apparatus 102 repeats simulations, while appropriately changing the conditions of a treatment plan, in accordance with evaluations based on various kinds of skin-dose displays by the skin dose evaluation support apparatus 320, and can obtain a desirable result through a small number of simulations.

Embodiment 2

Figure 9:
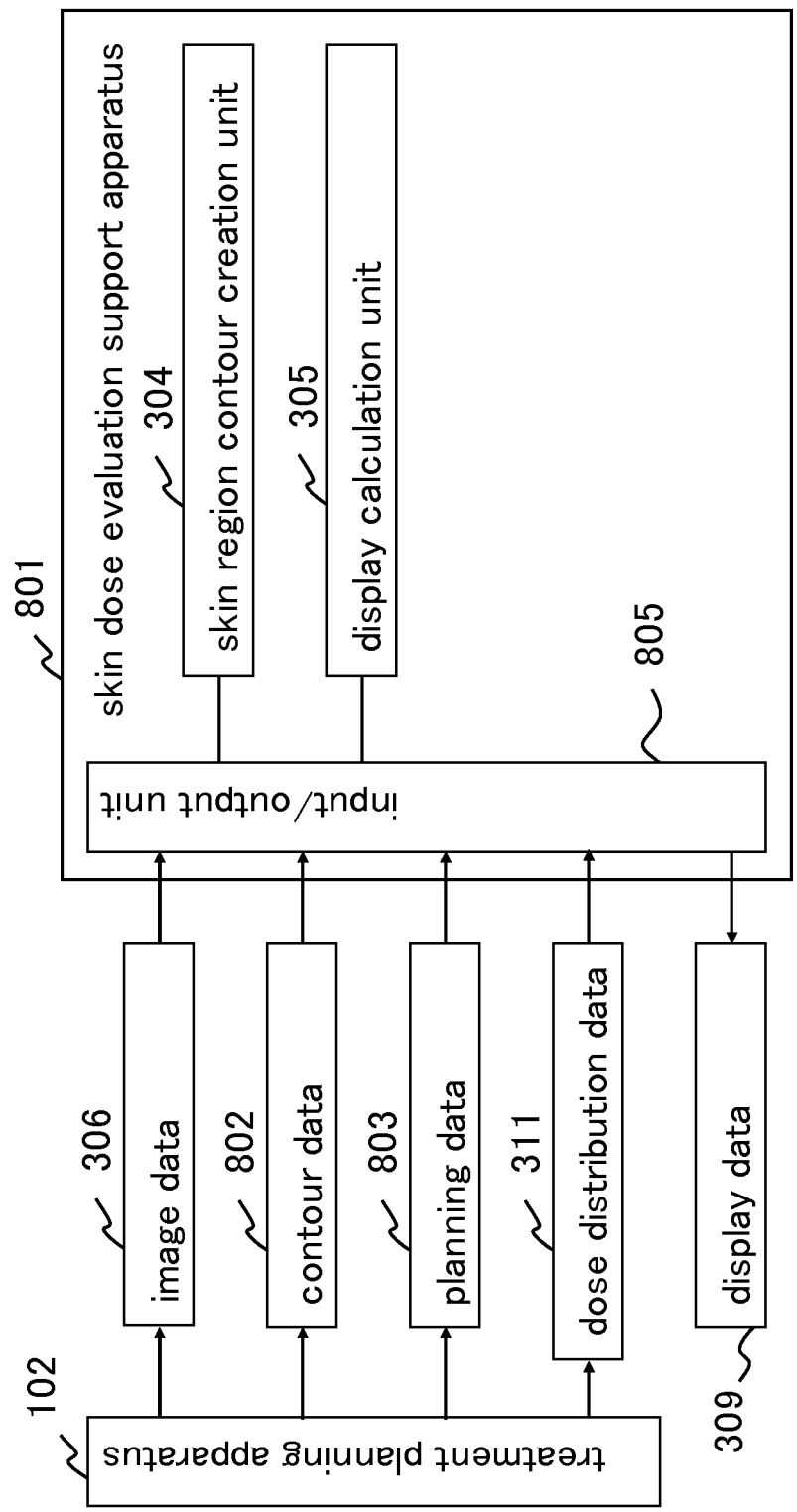
FIG. 9 is a diagram representing the configuration of a skin dose evaluation support apparatus according to Embodiment 2 of the present invention.

In Embodiment 1, an example has been explained in which the treatment planning apparatus 102 is provided with the skin dose evaluation support apparatus 320. In Embodiment 2, an example will be explained in which the treatment planning apparatus 102 and a skin dose evaluation support apparatus are separated from each other. FIG. 9 is a diagram representing the configuration of a skin dose evaluation support apparatus according to Embodiment 2 of the present invention. The skin dose evaluation support apparatus 801 has an input/output unit 805, the skin region contour creation unit 304, and the display calculation unit 305. By way of the input/output unit 805, the skin dose evaluation support apparatus 801 receives the image data 306, contour data 802, planning data 803, and the dose distribution data 311, which are each in a DICOM data format, from the treatment planning apparatus 102. As represented in FIG. 2, the skin dose evaluation support apparatus 801 is formed of a computer system. The treatment planning apparatus 102 according to Embodiment 2 corresponds to an apparatus that is obtained by removing the skin region contour creation unit 304 from the treatment planning apparatus 102 according to Embodiment 1.

The contour data 802 is data on a tissue region set by the tissue region setting unit 302 in the treatment planning apparatus 102. The planning data 803 is an irradiation condition for which the treatment planning apparatus 102 has implemented a simulation; the dose distribution data 311 is dose distribution data for which the treatment planning apparatus 102 has implemented a simulation and a calculation. In the skin dose evaluation support apparatus 801, the skin region contour creation unit 304 automatically creates the skin region contour 402 inside the body contour 401 (several pixels inward from the body contour). The display calculation unit 305 implements display processing items such as a three-dimensional display, an isodose chart display, and a DVH display of a conventional marker tissue, a normal tissue, or the whole human body tissue taken by a CT apparatus and implements display processing items such as a three-dimensional display, an isodose chart display, a DVH display and a DAH display of a skin region created by the skin region contour creation unit 304. The input/output unit 805 outputs to the display device 203 and the storage device 204 the display data 309 that has been processed and created by the display calculation unit 305.

Because being separated from the treatment planning apparatus 102, the skin dose evaluation support apparatus 801 according to Embodiment 2 can readily be expanded without a large modification added to an existing treatment planning apparatus. Therefore, it is made possible to demonstrate the effects explained in Embodiment 1 while utilizing an existing treatment planning apparatus. The skin dose evaluation support apparatus 801 according to Embodiment 2 can visually display a skin dose; therefore, it is made possible to accurately and intuitively grasp a skin dose when a treatment plan is created.

Embodiment 3

Figure 10:
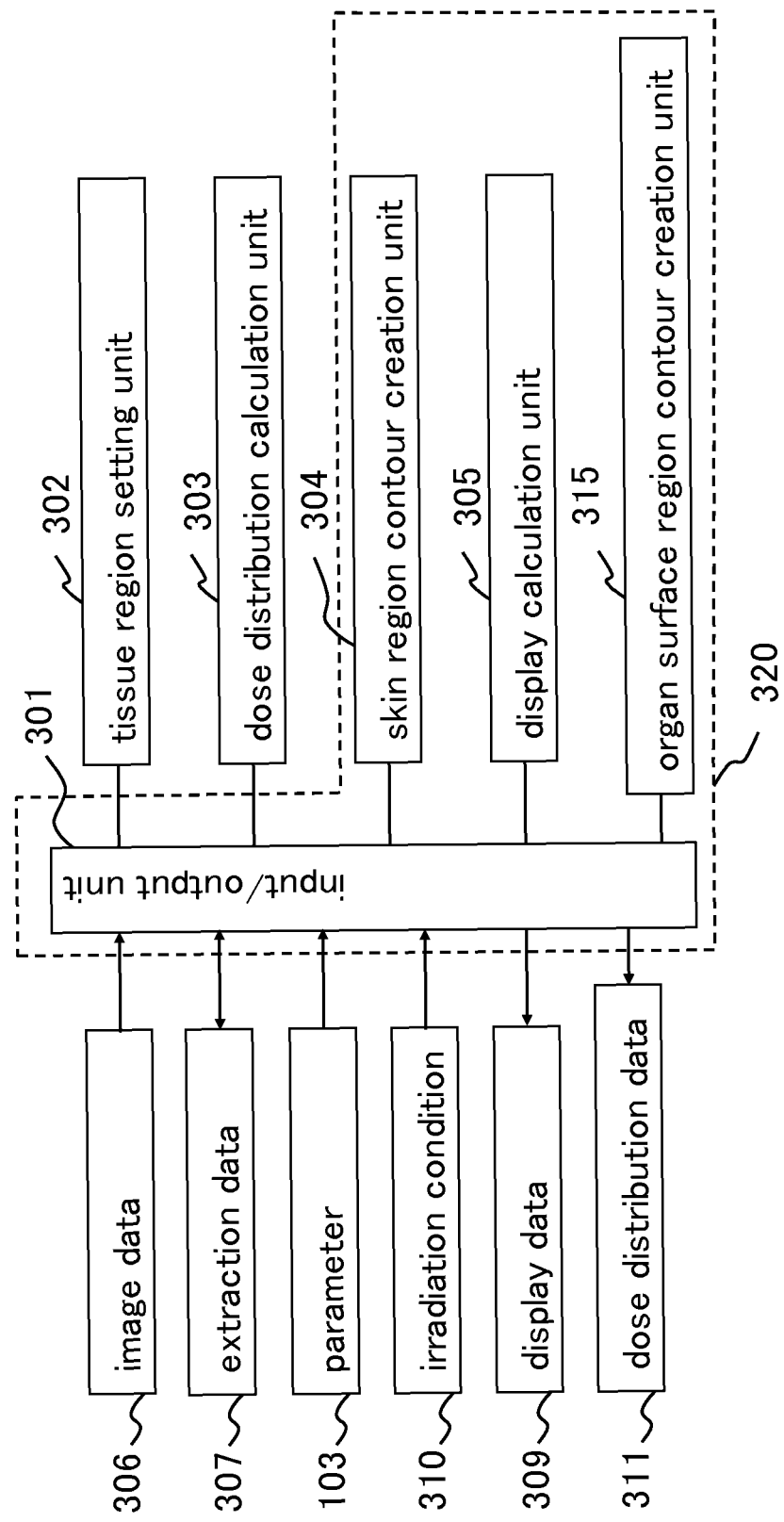
FIG. 10 is a diagram representing the configuration of a skin dose evaluation support apparatus according to Embodiment 3 of the present invention.
Figure 11:
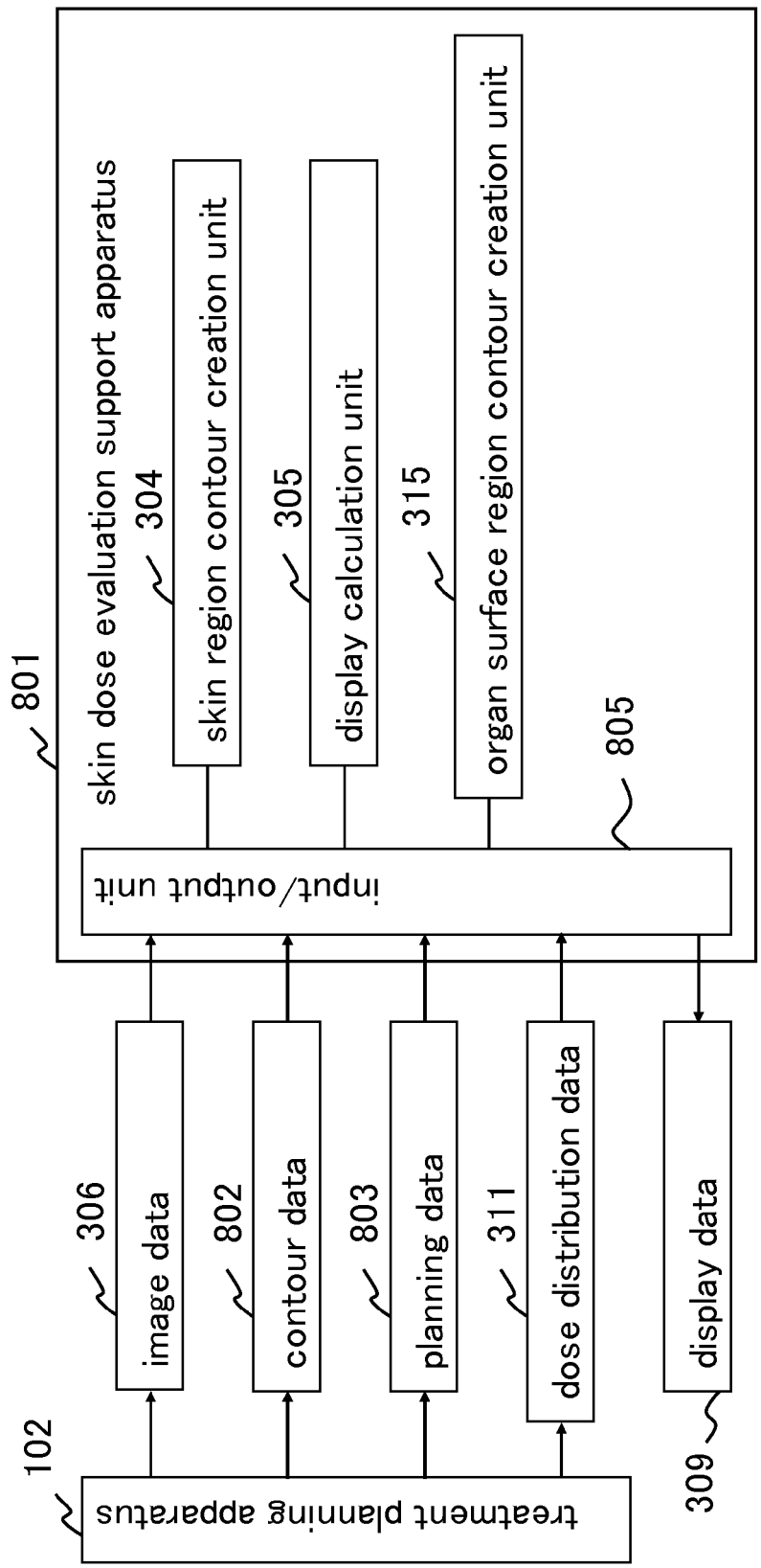
FIG. 11 is a diagram representing the configuration of another skin dose evaluation support apparatus according to Embodiment 3 of the present invention.

The dose evaluation technology in the skin dose evaluation support apparatus 320 according to Embodiment 1 or the skin dose evaluation support apparatus 801 according to Embodiment 2 can be applied also to a specified major organ. Embodiment 3 is an example in which the dose evaluation technology for a skin dose is applied also to a specified major organ. FIG. 10 is a diagram representing the configuration of a skin dose evaluation support apparatus according to Embodiment 3 of the present invention; FIG. 11 is a diagram representing the configuration of another skin dose evaluation support apparatus according to Embodiment 3 of the present invention. In the skin dose evaluation support apparatus according to Embodiment 3, an organ surface region contour creation unit 315 is added. The organ surface region contour creation unit 315 is to automatically create a contour for major organ surface dose evaluation and has the same function as the skin region contour creation unit 304 has.

The organ surface region contour creation unit 315 creates surface region information on an organ surface region surrounded by a tissue region (outer contour) set in the tissue region setting unit 302 and contour information (inner contour) for major organ surface dose evaluation, created in the organ surface region contour creation unit 315. The surface region information corresponds to the skin region information. Each of the skin dose evaluation support apparatuses 320 and 801 displays on the display device 203 a surface region dose of the surface region of a specified major organ in display formats such as a three-dimensional display, a cross section isodose chart display, a DVH display, and a DAH display. In the case of an intestinal-system organ such as a stomach, a small intestine, a large intestine, or a rectum, the surface region dose becomes large; therefore, the risk of a stomach ulcer or gastrointestinal bleeding is raised. Accordingly, by applying the dose evaluation technology of each of the skin dose evaluation support apparatuses 320 and 801 to a major organ, the dose on the surface region of a specified major organ can visually be displayed; therefore, it is made possible to accurately and intuitively grasp a surface region dose when a treatment plan is created. Moreover, it is made possible to create a treatment plan that can reduce as much as possible the disorder such as a stomach ulcer in the surface region of the major organ.

As described above, each of the skin dose evaluation support apparatuses 320 and 801 according to Embodiment 3 is provided with the organ surface region contour creation unit 315 that creates surface region information including the boundary coordinates of an organ surface region, which is the surface region of an organ of a patient, based on the image data 306 to be inputted when a treatment plan for a radiation therapy for a patient is created; and the display calculation unit 305 that extracts the organ surface dose in the organ surface region, based on the dose distribution data 311 calculated by the dose distribution calculation unit 303 of the treatment planning apparatus 102 and the skin region information, and creates display data for displaying the extracted organ surface dose in a predetermined display format. By displaying in a predetermined display format the organ surface dose in an organ surface region, which is extracted based on the dose distribution data 311 and the organ surface region information, it is made possible to visually display the organ surface dose; therefore, the organ surface dose can accurately and intuitively be grasped when a treatment plan is created.

The treatment planning apparatus 102 according to Embodiment 3 is provided with the tissue region setting unit 302 that obtains the three-dimensional coordinates of a body contour, a major organ, and a focus, which is a treatment subject, based on the image data 306 of a patient, the dose distribution calculation unit 303 that calculates the distribution of doses on the patient, based on a model in accordance with a radiation utilized in a radiation therapy, and the skin dose evaluation support apparatus 320 that displays on the display device 203 the skin dose in a skin region of the patient and the surface region dose in the surface region of an organ of the patient; the skin dose evaluation support apparatus 320 is provided with the skin region contour creation unit 304 that creates skin region information including the boundary coordinates of a skin region, based on the image data 306, the organ surface region contour creation unit 315 that creates surface region information including the boundary coordinates of an organ surface region, which is the surface region of an organ of a patient, based on the image data 306 to be inputted when a treatment plan for a radiation therapy for a patient is created, and the display calculation unit 305 that extracts the skin dose in a skin region, based on the dose distribution data 311 calculated by the dose distribution calculation unit 303 and the skin region information, and extracts the organ surface dose in an organ surface region, based on the dose distribution data 311 and the surface region information, and creates display data for displaying the extracted skin dose and the surface region dose in a predetermined display format. As a result, the skin dose evaluation support apparatus 320 makes it possible to accurately and intuitively grasp a skin dose and a surface region dose; thus, there can be created a treatment plan that can diminish as much as possible troubles such as a skin inflammation and a stomach ulcer in the surface region of a major organ. Moreover, the treatment planning apparatus 102 repeats simulations, while appropriately changing the conditions of a treatment plan, in accordance with evaluations based on various kinds of skin-dose displays by the skin dose evaluation support apparatus 320, and can obtain a desirable result through a small number of simulations.

The apparatus in which the dose evaluation technology of the skin dose evaluation support apparatus 320 or 801 is applied to a major organ may be referred to as a surface region dose evaluation support apparatus.

The skin dose evaluation support apparatus 320 and the treatment planning apparatus 102 according to Embodiment 1, the skin dose evaluation support apparatus 801 according to Embodiment 2, and the skin dose evaluation support apparatuses 320 and 801 and the treatment planning apparatus 102 according to Embodiment 3 can be applied not only to a foregoing radiation therapy system in which an X ray or a particle beam such as a proton beam or a carbon beam is utilized but also to a radiation therapy system in which a gamma ray or a charged particle such as an electron beam or the like is utilized.

DESCRIPTION OF REFERENCE NUMERALS

102: treatment planning apparatus
203: display device
302: tissue region setting unit
303: dose distribution calculation unit
304: skin region contour creation unit
305: display calculation unit
306: image data
309: display data
311: dose distribution data
315: organ surface region contour creation unit
320: skin dose evaluation support apparatus
401: body contour
404: major organ
405: major organ
502: pointer
504: body contour assembly (human body image)
603: DVH characteristic curve
701: DAH characteristic curve
801: skin dose evaluation support apparatus

The invention claimed is:

1. A non-transitory computer readable medium having instructions stored thereon for causing a computer to execute a skin dose evaluation support program that displays on a display device a skin dose in a skin region of a patient, comprising the steps of:
    creating skin region information including boundary coordinates of the skin region, based on image data input when a treatment plan for a radiation therapy for the patient is created, and
    extracting the skin dose in the skin region, based on dose distribution data calculated by a treatment planning apparatus and the skin region information, and
    creating display data for displaying the extracted skin dose in a predetermined display format.

2. The non-transitory computer readable medium according to claim 1, wherein the creating step comprises creating display data for displaying, in a three-dimensional manner, a distribution of the skin dose in such a way as to be superimposed on a human image displayed in a three-dimensional manner.

3. The non-transitory computer readable medium according to claim 2, wherein when in the skin dose distribution displayed on a display device and a pointer specifies a display point, the comprising the step of: displaying on the display device a value of the skin dose corresponding to the display point.

4. The non-transitory computer readable medium according to claim 1, creating step comprises creating display data for displaying a distribution of the skin dose in such a way as to be superimposed on a specified cross section of the patient.

5. The non-transitory computer readable medium according to claim 1, further comprising the steps of:
    creating a first Dose Volume Histogram ("DVH"), which is a graph representing a relationship between the skin dose in the skin region and a volume of a tissue indicating a value of the skin dose, and
    causing a display of the first DVH on the display device.

6. The non-transitory computer readable medium according to claim 1, further comprising the steps of:
    creating a first Dose Area Histogram ("DAH"), which is a graph representing a relationship between the skin dose in the skin region and an area indicating a value of the skin dose, and
    causing a display of the first DAH on the display device.

7. The non-transitory computer readable medium according to claim 1, wherein the creating the skin region information is based on information on a body contour set in the image data.

8. The non-transitory computer readable medium according to claim 1, further comprising the step of:
    creating surface region information including boundary coordinates of an organ surface region, which is the surface region of an organ of the patient, based on the image data, by extracting a surface region dose in the organ surface region, based on the dose distribution data and the surface region information, and creating display data for displaying, on the display device, the extracted surface region dose, in a predetermined display format.

9. The non-transitory computer readable medium according to claim 8, comprising the step of: creating display data for displaying, in a three-dimensional manner, a distribution of the surface region dose in such a way as to be superimposed on a human image displayed in a three-dimensional manner.

10. The non-transitory computer readable medium according to claim 8, comprising the step of: creating display data for displaying a distribution of the surface region dose in such a way as to be superimposed on a specified cross section of the patient.

11. The non-transitory computer readable medium according to claim 9, wherein when in a distribution of the surface region dose displayed on the display device, a pointer specifies a display point, comprising the step of: displaying on the display device a value of the surface region dose corresponding to the display point.

12. The non-transitory computer readable medium according to claim 8, comprising the steps of:
    creating a second Dose Volume Histogram ("DVH"), which is a graph representing a relationship between the surface region dose in the organ surface region and a volume of a tissue indicating a value of the surface region dose, and causing a display of the second DVH on the display device.

13. The non-transitory computer readable medium according to claim 8, comprising the steps of:
    creating a second Dose Area Histogram ("DAH"), which is a graph representing a relationship between the surface region dose in the organ surface region and an area indicating a value of the surface region dose, and
    causing a display of the second DAH on the display device.

14. The non-transitory computer readable medium according to claim 8, comprising the creating of the surface region information is based on information on an outer contour set in the image data.

15. A treatment planning apparatus that creates a treatment plan for a radiation therapy for a patient, comprising:
a display device,
the non-transitory computer readable medium of claim 8; and
a processor configured to:
obtain three-dimensional coordinates of a body contour, a major organ, and a focus, which is a treatment subject, based on image data on the patient;
calculate a dose distribution on the patient, based on a model in accordance with a radiation utilized in the radiation therapy; and
execute the skin dose evaluation support program according to claim 8.

16. A treatment planning apparatus that creates a treatment plan for a radiation therapy for a patient, comprising:
a display device;
the non-transitory computer readable medium of claim 1; and
a processor configured to:
obtain three-dimensional coordinates of a body contour, a major organ, and a focus, which is a treatment subject, based on image data on the patient;
calculate a dose distribution on the patient, based on a model in accordance with a radiation utilized in the radiation therapy; and
execute the skin dose evaluation support program according to claim 1.

* * * * *